United States Patent
Arslantas et al.

(10) Patent No.: US 7,923,558 B2
(45) Date of Patent: Apr. 12, 2011

(54) METHOD FOR OBTAINING PURE TETRAHYDROCANNABINOL

(75) Inventors: Enver Arslantas, Constance (DE); Ulrich Weigl, Hilzingen (DE)

(73) Assignee: Cilag Ltd., Schaffhausen (CH)

( * ) Notice: Subject to any disclaimer, the term of this patent is extended or adjusted under 35 U.S.C. 154(b) by 1006 days.

(21) Appl. No.: 11/571,864

(22) PCT Filed: Jul. 19, 2004

(86) PCT No.: PCT/CH2004/000458
§ 371 (c)(1),
(2), (4) Date: May 10, 2007

(87) PCT Pub. No.: WO2006/007734
PCT Pub. Date: Jan. 26, 2006

(65) Prior Publication Data
US 2008/0275237 A1 Nov. 6, 2008

(51) Int. Cl.
*C07D 405/04* (2006.01)
*C07D 213/26* (2006.01)
*C07D 231/02* (2006.01)
*C07D 311/80* (2006.01)

(52) U.S. Cl. .................. 544/375; 546/258; 548/364.4; 548/525; 549/390

(58) Field of Classification Search .................. 544/375; 549/390; 546/258; 548/364.4, 525
See application file for complete search history.

(56) References Cited

U.S. PATENT DOCUMENTS

| | | |
|---|---|---|
| 3,560,528 A | 2/1971 | Petrzilka |
| 3,668,224 A | 6/1972 | Petrzilka |
| 3,941,782 A | 3/1976 | Harris et al. |
| 4,025,630 A | 5/1977 | Dren et al. |
| 4,179,517 A | 12/1979 | Mechoulam et al. |
| 4,381,399 A | 4/1983 | Olsen et al. |
| 4,933,363 A | 6/1990 | ElSohly |

FOREIGN PATENT DOCUMENTS

| | | |
|---|---|---|
| DE | 2106705 | 8/1971 |
| WO | WO 94/27533 A1 | 12/1994 |
| WO | WO 2004/043946 A1 | 5/2004 |

*Primary Examiner* — James O Wilson
*Assistant Examiner* — Ebenezer Sackey
(74) *Attorney, Agent, or Firm* — Hammer & Associates, P.C.

(57) ABSTRACT

The invention relates to a method for obtaining pure tetrahydrocannabinol from reaction mixtures containing tetrahydrocannabinol compounds or from raw products containing tetrahydrocannabinol compounds. According to said method, the tetrahydrocannabinol compounds in the reaction mixture or in the raw product are converted into crystallisable derivatives, preferably using a suitable solvent, said derivatives are then crystallised and isolated, and the pure tetrahydrocannabinol compounds are then obtained from the crystallised derivatives. The invention also related to the use of compounds produced in this way for the production of a medicament for human therapy, and to the medicaments thus produced.

17 Claims, No Drawings

METHOD FOR OBTAINING PURE TETRAHYDROCANNABINOL

The present invention relates to a process for obtaining pure tetrahydrocannabinol, particularly for obtaining pure $\Delta^8$-tetrahydrocannabinol ($\Delta^8$-THC) and pure $\Delta^9$-tetrahydrocannabinol ($\Delta^9$-THC), and very particularly for obtaining stereospecifically (enantiomerically) pure (−)-$\Delta^8$-THC and stereospecifically (enantiomerically) pure (−)-$\Delta^9$-THC.

$\Delta^8$-Tetrahydrocannabinol ($\Delta^8$-THC) and $\Delta^9$-tetrahydrocannabinol ($\Delta^9$-THC) are known compounds and can be obtained e.g. as an extract of the plant Cannabis sativa L. Chemical syntheses for these compounds are also known. U.S. Pat. No. 3,560,528 describes a process for the preparation of $\Delta^8$-THC by reacting trans-p-mentha-2,8-dien-1-ol with 3-n-pentylresorcinol (olivetol) in the presence of a catalytically active compound. U.S. Pat. No. 3,668,224 describes the preparation of $\Delta^9$-THC by adding e.g. hydrogen chloride onto the $\Delta^8$ double bond of $\Delta^8$-THC, the chlorine atom bonding in the 9-position, and then eliminating hydrogen chloride to form $\Delta^9$-THC.

The normal procedure in the preparation of $\Delta^8$-THC and $\Delta^9$-THC is to isolate $\Delta^8$-THC and $\Delta^9$-THC from the reaction mixture with a suitable organic solvent and then optionally remove the solvent. This gives $\Delta^8$-THC or $\Delta^9$-THC as "crude product" dissolved in a solvent or in an oily form without solvent. The impurities present in these crude products containing $\Delta^8$-THC or $\Delta^9$-THC are predominantly educts and reaction by-products (e.g. isomers), from which $\Delta^8$-THC or $\Delta^9$-THC has to be separated.

In the known processes, the THC compounds prepared as crude products in this way are purified by chromatographic methods and/or distillation. However, these methods are normally unsuitable for the purification of THC compounds on the industrial scale. Chromatographic separation requires a very large amount of solvent, whose subsequent removal is expensive. Distillative separation in turn has the disadvantage that the isomeric THC compounds to be separated are very similar to one another both in their boiling points and in their polarities, so very high demands have to be made on the separation efficiency of the equipment. This reduces the material throughput and, even when the separation efficiency is high, "mixed fractions" are obtained in relatively large amounts, markedly reducing the yield. These THC compounds also have comparatively high boiling points in the region of 150° C. at 0.02 Torr. A distillation therefore requires special technical facilities. In addition, due to the high temperatures, a partial decomposition and/or isomerization of the THC compounds takes place to the extent of around 18% by weight on the laboratory scale. For longer heating times on a larger scale, a higher decomposition/isomerization rate is thus to be expected.

It has now been found that tetrahydrocannabinol compounds, especially $\Delta^8$-THC and $\Delta^9$-THC, can be converted to crystallizable derivatives directly in the reaction mixture or already present as "crude product", preferably using a suitable solvent; said derivatives crystallize out in very pure form and their crystallization and purification are technically simple to carry out. From the compounds crystallized in this way, the pure tetrahydrocannabinol compounds, especially pure $\Delta^8$-THC or pure $\Delta^9$-THC, can be obtained in very high purity by chemical methods known per se and conventional extractive purification. This substantially simplifies the recovery of pure tetrahydrocannabinol compounds, such as pure $\Delta^8$-THC or $\Delta^9$-THC, and an expensive chromatographic or distillative separation is not necessary. It is also advantageous that the process according to the invention can be applied to any appropriate crude products, independently of the particular synthesis used.

The present invention relates to a process for obtaining pure tetrahydrocannabinol from reaction mixtures containing tetrahydrocannabinol compounds or from crude product containing tetrahydrocannabinol compounds, characterized in that the tetrahydrocannabinol compound in the reaction mixture or in the crude product is converted to a crystallizable derivative, preferably using a suitable solvent, said derivative is crystallized out and isolated and the pure tetrahydrocannabinol compound is then obtained from the crystallized derivative.

The pure tetrahydrocannabinol compound is obtained in this process as a colorless oil that solidifies to a glass on cooling. No other purification steps, e.g. distillation or preparative HPLC, are required.

The tetrahydrocannabinol compound is preferably $\Delta^8$-THC or $\Delta^9$-THC. In this sense the present invention preferably relates to a process for obtaining pure $\Delta^8$-THC or $\Delta^9$-THC from a reaction mixture or crude product containing $\Delta^8$-THC and/or $\Delta^9$-THC, by converting the $\Delta^8$-THC or $\Delta^9$-THC contained therein to a crystallizable derivative, crystallizing out and isolating said derivative and then obtaining the pure $\Delta^8$-THC or the pure $\Delta^9$-THC from the crystallized derivative. It is preferable to obtain stereospecifically (enantiomerically) pure $\Delta^8$-THC and stereospecifically (enantiomerically) pure $\Delta^9$-THC.

The present invention further relates to the pure tetrahydrocannabinol compounds prepared in this way, especially the pure compounds $\Delta^8$-THC and $\Delta^9$-THC prepared according to the invention.

The present invention further relates to the crystallizable derivatives of the tetrahydrocannabinol compounds used as intermediates, and to the crystallized derivatives of the tetrahydrocannabinol compounds, especially those of $\Delta^8$-THC and $\Delta^9$-THC, used as intermediates.

The present invention further relates to the use of the compounds prepared according to the invention for the preparation of a drug for human therapy, and to the drugs prepared in this way.

"Tetrahydrocannabinol compounds" are to be understood as meaning compounds of formulae (I) and (IA) below:

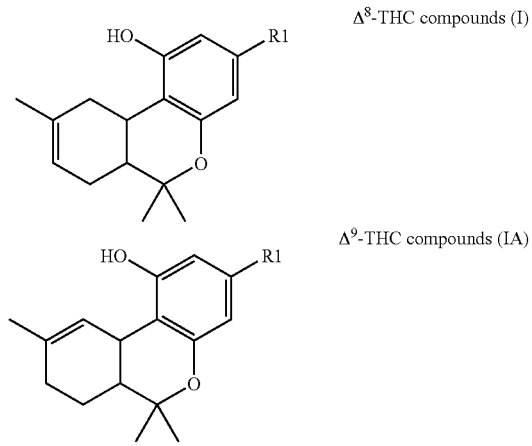

in which $R_1$ is hydrogen, chlorine or ($C_{1-10}$)-alkyl, preferably n-$C_5H_{11}$.

Preferred compounds are those of formulae (I') and (I'A):

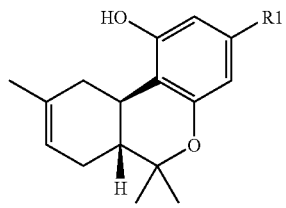

Δ⁸-THC compounds (I')

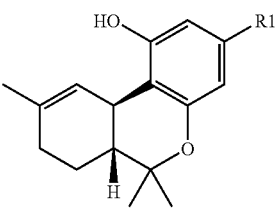

Δ⁹-THC compounds (I'A)

in which $R_1$ is as defined above.

The synthesis of crystallizable derivatives of tetrahydrocannabinol compounds is described below using Δ⁸-THC and Δ⁹-THC as examples, but the description analogously includes other known tetrahydrocannabinol compounds.

Crystallizable derivatives of tetrahydrocannabinol compounds which can be prepared in almost quantitative yield and can be crystallized from solutions are e.g. the 2-naphthoyl ester of Δ⁸-THC of formula (II) and the 2-naphthoyl ester of Δ⁹-THC of formula (IIA):

Δ⁸-THC:

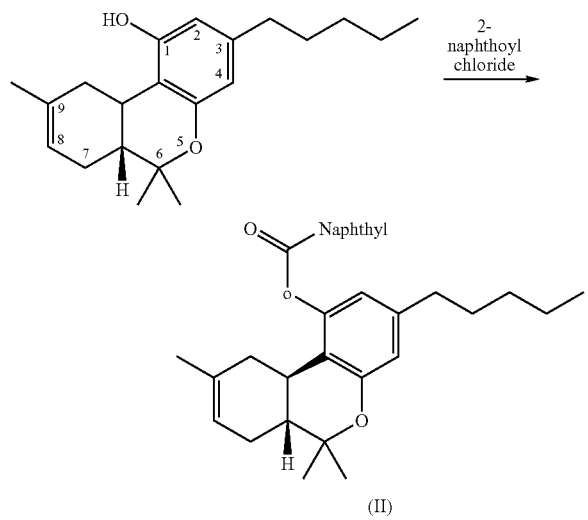

(II)

Δ⁹-THC:

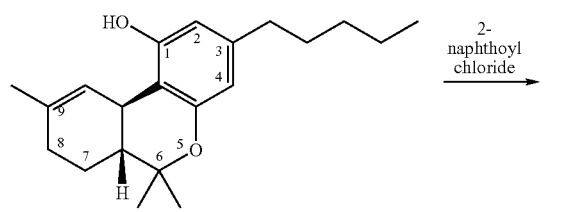

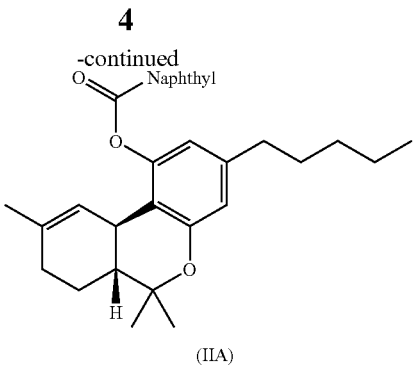

(IIA)

Said naphthoyl radical can be substituted, e.g. by nitro, bromo or methyl groups, preferably in the 5- or 8-position. The corresponding substituted 1-naphthoyl compounds may also exist. Correspondingly, the naphthyl radicals and polycyclic carboxylic acid derivatives bonded as amides, e.g. derivatives of 9-anthracene-carboxylic acid or 9-phenanthrenecarboxylic acid, optionally substituted analogously to the naphthoyl derivatives, are also crystallizable.

Esters and amide compounds of Δ⁸-THC and Δ⁹-THC which contain a group capable of salt formation in the ester or amide substituent, e.g. a carboxyl group or an amine grouping, are also suitable for carrying out the process according to the invention.

The crystallizable tetrahydrocannabinol compounds which can be used in the process according to the invention are covered by formulae (III) and (IIIA) below:

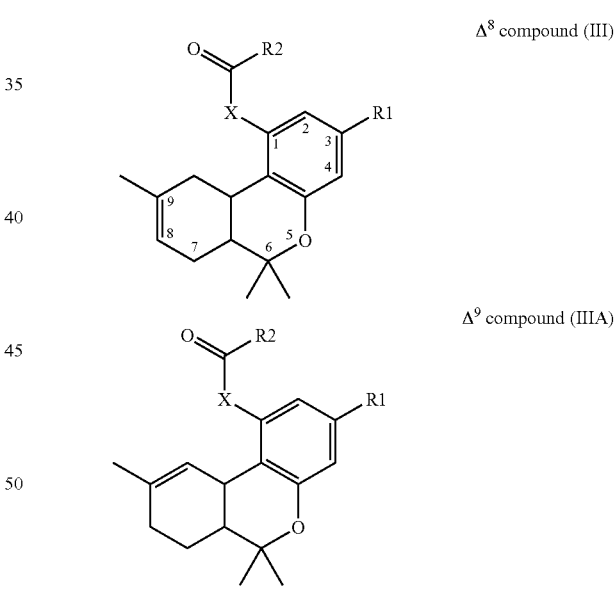

in which
$R_1$ is hydrogen, chlorine or $(C_{1-10})$-alkyl, preferably n-$C_5H_{11}$;
X is —O— or —NH—, preferably —O— (oxygen); and
$R_2$ is an optionally substituted aliphatic or aromatic radical which optionally carries a substituent capable of salt formation; or a heterocyclic radical which optionally is itself capable of salt formation and/or optionally carries a substituent capable of salt formation; or a radical of an aliphatic or aromatic polybasic acid, preferably a dibasic acid, wherein the acid group not bonded to the THC derivative preferably forms a radical capable of salt formation, or is bonded to such a radical, or the compound is a salt.

Preferred compounds are those of formulae (III') and (III'A):

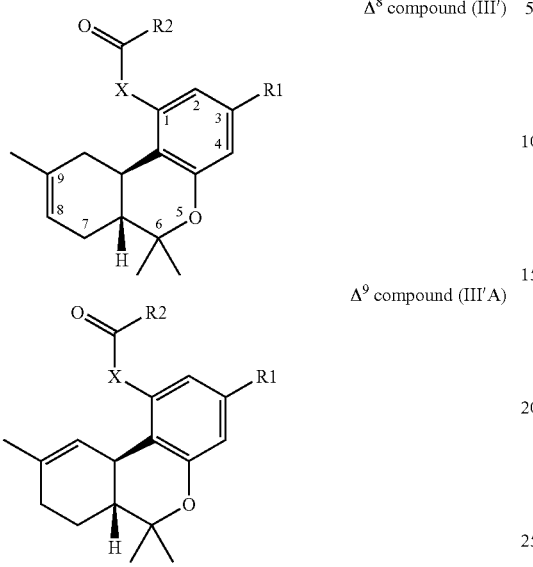

Δ⁸ compound (III')

Δ⁹ compound (III'A)

in which the substituents are as defined above.

$R_1$ as $(C_{1-10})$-alkyl is preferably methyl, ethyl, propyl, butyl, pentyl or hexyl, preferably n-$C_5H_{11}$.

$R_2$ as an aliphatic radical preferably carrying a radical capable of salt formation is preferably methyl, ethyl, propyl, butyl, benzyl, aminobenzyl, cyclopentyl or cyclohexyl that is optionally correspondingly substituted.

$R_2$ as an aromatic radical optionally carrying a substituent capable of salt formation is preferably phenyl optionally substituted by nitro, halogen, methyl or sulfonyl, or naphthyl optionally substituted by nitro, halogen, methyl or sulfonyl, preferably unsubstituted naphthyl.

$R_2$ as a heterocyclic radical that is itself optionally capable of salt formation and/or optionally carries a substituent capable of salt formation is e.g. a 2-pyridyl, 3-pyridyl or 4-pyridyl derivative or a corresponding picoline, pyrazine, pyrazole, pyrrole or indole derivative, preferably a substituent derived from pyridinecarboxylic acid or pyridinedicarboxylic acid.

$R_2$ as a radical of an aliphatic polybasic acid, preferably a dibasic saturated or unsaturated acid, is preferably a radical of an acid of the formula —O(O)C—(CH$_2$)$_n$—C(O)OH or —O(O)C—CH=CH—C(O)OH, e.g. the radical of oxalic acid, malonic acid, succinic acid, fumaric acid, maleic acid, tartaric acid, malic acid or an analogous acid, wherein the acid group not bonded to the THC derivative optionally forms a radical capable of salt formation, or is bonded to such a radical. $R_2$ can also be e.g. asparagine [—O(O)C—CH(NH$_2$)—CH$_2$CONH$_2$] or aspartic acid [—O(O)C—CH(NH$_2$)CH$_2$—C(O)OH].

$R_2$ as a radical of an aromatic dicarboxylic or polycarboxylic acid is preferably the radical of phthalic acid or terephthalic acid, wherein the acid group not bonded to the THC derivative is optionally bonded to a radical capable of salt formation.

Thus the acid group not bonded to the THC derivative can be coupled e.g. with a diamine by means of an amide linkage. In this way salt formation can take place with the radical capable of salt formation, or with the diamine radical, and, for example, the corresponding hydrochloride or hydrobromide, nitrate, oxalate or salts with methylsulfonic acid, toluenesulfonic acid or benzenesulfonic acid can be formed.

Thus, for example, the following Δ⁹-THC derivative can be prepared, as the base or a salt, and crystallized in pure form, it then being possible to recover the pure Δ⁹-THC from the derivative by hydrolysis known per se:

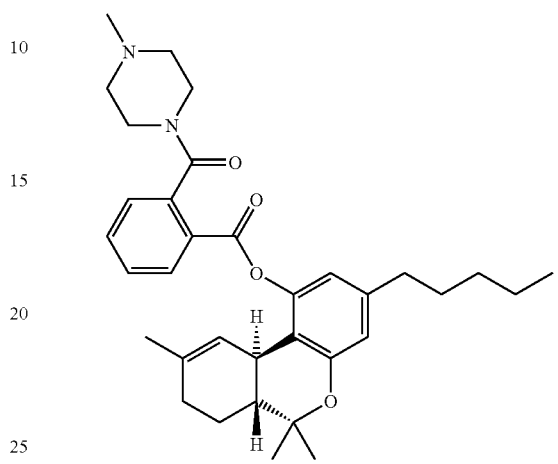

In this sense the following derivatives of tetrahydrocannabinol compounds, preferably of Δ⁸-THC and Δ⁹-THC, are preferred: esters with 1-naphthoic acid, 2-naphthoic acid, 1-naphthylacetic acid or 2-naphthylacetic acid, their naphthalene radical optionally being substituted. Such substituents are preferably bromo, nitro and methyl, preferably in the 5- or 8-position.

Ester derivatives of tetrahydrocannabinol compounds, preferably of Δ⁸-THC and Δ⁹-THC, with polycyclic carboxylic acids such as 9-anthracenecarboxylic acid or 9-phenanthrenecarboxylic acid, whose anthracene radical or phenanthrene radical is optionally substituted, are also preferred. Ester derivatives with 1-naphthoic acid or 2-naphthoic acid ester, especially 2-naphthoic acid ester, are particularly preferred.

Salts of ester derivatives of tetrahydrocannabinol compounds, preferably of Δ⁸-THC and Δ⁹-THC, with dicarboxylic acids such as phthalic acid, terephthalic acid or oxalic acid, with a suitable counterion as cation, are also preferred, said cation preferably being an alkali metal or alkaline earth metal ion, preferably Na⁺, K⁺, Ca²⁺ or Mg²⁺, or ammonium, or a primary, secondary or tertiary ammonium ion. Examples of suitable ammonium ions are the cations of the following amines: dibenzylamine, tert-butylamine, choline, trishydroxymethylamine and ethylenediamine.

Salts of ester derivatives of tetrahydrocannabinol compounds, preferably of Δ⁸-THC and Δ⁹-THC, with dicarboxylic acids such as phthalic acid, terephthalic acid or oxalic acid, which, at the free carboxyl group (carboxyl group not bonded to the THC derivative), are coupled with a diamine, preferably piperazine or N-methylpiperazine, via an amide linkage, are also preferred, as well as the salt, preferably as the hydrochloride, hydrobromide, nitrate, oxalate, tosylate, mesylate or besylate. The corresponding N-methylpiperazine derivative of phthalic acid, as the hydrochloride, is preferred.

The procedure for preparing the tetrahydrocannabinol compounds is e.g. to react olivetol with menthadienol [(+)-p-mentha-2,8-dien-1-ol] in the presence of an acidic catalyst, preferably p-toluenesulfonic acid or BF$_3$.Et$_2$O, at elevated temperature, preferably above 50° C. (>50° C.) and preferably above 80° C. (>80° C.), in an unreactive organic solvent, e.g. toluene, to give $\Delta^8$-THC (or $\Delta^9$-THC in the case of $BF_3.Et_2O$). Washing of the reaction mixture with aqueous buffer solution and concentration of the toluene phase gives crude $\Delta^8$-THC (or $\Delta^9$-THC in the case of $BF_3.Et_2O$) with a purity of 50-55%. It is not necessary to protect any reactive groups (literature: Petrzilka, Helvetica Chimica Acta 1969, 52, 1102; Radzan, J. Am. Chem. Soc. 1974, 96, 5860; patent literature cited above).

To prepare the derivative, e.g. $\Delta^8$-THC naphthoyl ester, the crude $\Delta^8$-THC is dissolved in a water-immiscible aprotic solvent and converted to the ester with a desired naphthoyl chloride using a base, preferably a tertiary amine, at 0-100° C., preferably at 20-25° C. The reaction mixture is washed with aqueous buffer solution. The addition of methanol or another suitable alcohol precipitates the $\Delta^8$-THC naphthoyl ester out of the solvent. The crude $\Delta^8$-THC naphthoyl ester can be recrystallized from a selection of organic solvents (e.g. acetonitrile).

To recover $\Delta^8$-THC from the $\Delta^8$-THC naphthoyl ester, the latter is saponified at 0-100° C., preferably at room temperature, in a mixture of water-miscible solvents (e.g. TBF and/or alcohols and/or acetone) and water, with a strong base that is soluble in this solvent mixture (e.g. sodium hydroxide or diethylamine), preferably with hydroxide bases. After neutralization with acid, the organic solvent is distilled out of the reaction mixture and the aqueous-oily residue is extracted with a water-immiscible solvent (e.g. a hydrocarbon). The $\Delta^8$-THC is obtained after evaporation of the organic phase.

Crude $\Delta^9$-THC is preferably prepared by dissolving $\Delta^8$-THC in a water-immiscible solvent, e.g. ethyl acetate. The reaction mixture is saturated with HCl by the introduction of HCl gas. A Lewis acid, e.g. zinc chloride, is added and the reaction mixture is stirred at 0-50° C. The reaction mixture is then washed, firstly with water and then with aqueous buffer solution. The organic phase is evaporated and the residue is dissolved in a water-immiscible solvent, e.g. toluene. An excess of a solution of an alcoholate in the corresponding solvent, e.g. toluene, is added and the reaction mixture is heated until the elimination of HCl is complete. The reaction mixture is buffered and worked up under aqueous conditions. The crude $\Delta^9$-THC is obtained after evaporation of the organic phase (literature: Petrzilka, Helvetica Chimica Acta 1969, 52, 1102).

To prepare crude $\Delta^9$-THC naphthoyl ester, the crude $\Delta^9$-THC is dissolved in a non-polar aprotic organic solvent and esterified in the presence of amine bases with the corresponding naphthoyl chloride derivatives at 0-100° C., preferably at room temperature. After complete conversion, the precipitate formed is filtered off and the filtrate is washed with buffer solution. The organic phase is evaporated and the residue is dissolved in a suitable solvent, e.g. acetonitrile, with heating. The $\Delta^9$-THC naphthoyl ester crystallizes on cooling and is filtered off.

To enrich the $\Delta^9$-THC naphthoyl ester, the crude $\Delta^9$-THC naphthoyl ester (contains <5% of $\Delta^8$-THC naphthoyl ester) is dissolved in a suitable organic solvent, e.g. THF. The addition of a suitable alcohol precipitates the enriched $\Delta^9$-THC naphthoyl ester (reduction of the $\Delta^8$-THC naphthoyl ester by 25-90%, normally by approx. 50%).

To recover $\Delta^9$-THC from the $\Delta^9$-THC naphthoyl ester, the latter is dissolved in a suitable solvent, e.g. THF, and at least one equivalent of water, a strong base that is soluble therein, e.g. a diamine, is added and the mixture is stirred at 0-100° C., preferably at room temperature, until the ester cleavage is complete. A little water is then added and the $\Delta^9$-THC is extracted with a non-polar organic solvent, optionally after distillation of the solvent used for the ester cleavage. The organic phase is evaporated and dried under high vacuum.

The preparation of the THC compounds is extensively known per se from the literature. The ester formation can be carried out under analogous process conditions known per se for the reaction of an alcohol with an acid chloride or any other activated acid derivative (anhydride, bromide), with the addition of a base. The choice of base is largely arbitrary and is known from analogous processes. Suitable solvents are any aprotic solvents. It is possible in principle to use temperatures ranging from the melting points to the boiling points of the solvents (up to at least 100° C.).

The THC esters can be crystallized/recrystallized from suitable solvents or combinations of solvent/antisolvent. The solvents are substance-dependent. In principle, suitable solvents are aprotic solvents, preferably polar aprotic solvents (e.g. THF, acetonitrile, acetone).

Particularly suitable antisolvents are alcohols, e.g. polar alcohols such as methanol or ethanol, or higher (non-polar and polar) alcohols, and optionally also water (provided it is miscible with the solvent).

The compounds are preferably dissolved at elevated temperatures, e.g. the boiling point of the solvent. Temperatures below 30° C. (<30° C.) are preferred for crystallization. Isomers can be enriched by crystallization and recrystallization.

The ester cleavage takes place by the process known per se, whereby an ester and water are reacted with a strong base (pH>10, preferably pH>12). Suitable bases are inorganic bases (provided they are soluble in the chosen solvent) or amines. Because of the pH requirement, stronger amines, such as diamines, are preferred. Suitable solvents are any solvents in which ester, base and at least small amounts of water dissolve and which have an inert behavior in the chosen system. Preference is given to water-miscible solvents, such as alcohols, THF or acetonitrile, or poorly water-miscible solvents with a certain residual polarity (e.g. ether, dichloromethane, toluene). Temperatures ranging from the melting point to the boiling point of the solvent (up to at least 100° C.) are possible in principle.

The THC compounds are purified by being taken up in a water-immiscible solvent (either directly from the ester cleavage or, if the solvent used therein is water-soluble, by concentration of the reaction mixture, optionally after neutralization, and addition of a water-immiscible solvent), optionally with the addition of water. The impurities (base for ester cleavage, acid for neutralization, naphthoic acid anion) are then extracted into the aqueous phase. The solvent used for purification is preferably a hydrocarbon since this makes the separation of the impurities more effective. The organic phase is then concentrated and dried under vacuum to remove the extraction solvent.

The above details apply to the synthesis of THC esters of monoacids. The synthesis of THC esters with diacids or derivatives thereof also requires the addition of a counterion for the precipitation, the conditions being uncritical and known from analogous reactions, and the solvents may have to be modified, as mentioned previously in the text. This enables alcohols to change from non-solvents to solvents.

According to the invention, not all crude products, as described above, have to be isolated. Some of the process steps can be carried out as one-pot stages (depending on the ester derivative and the solvent). Thus, for example, distillation of the solvent after the ester cleavage is superfluous if a water-immiscible solvent is used for this purpose. The mother liquors can be recycled, e.g. by repeating the sequence of HCl addition and elimination, as described above.

The Examples which follow illustrate the invention.

EXAMPLE 1

Preparation of (−)-$\Delta^8$-6a,10a-trans-tetrahydrocannabinol 2-naphthoyl ester ($\Delta^8$ 2-naphth.)

A) Preparation of $\Delta^8$-THC:

24.2 g (0.154 mol) of trans-p-mentha-(2,8)-dien-1-ol are added dropwise at an internal temperature of 85° C. to a stirred mixture of 26.5 g (0.140 mol) of olivetol and 4.0 g (0.02 mol) of p-toluenesulfonic acid monohydrate in 650 g of toluene. After a total of 2.5 hours, the reaction mixture is allowed to cool to room temperature and washed with 300 ml of semisaturated NaHCO$_3$ solution, then with 150 ml of water and with 150 ml of saturated sodium chloride solution. The organic phase is dried over MgSO$_4$ and concentrated under reduced pressure to give a brownish oil (49.8 g), which contains 52% of $\Delta^8$-THC according to gas chromatography.

B) Preparation of crystalline $\Delta^8$ 2-naphth.

22.8 g of the crude product prepared in section A) (0.038 mol of $\Delta^8$-THC) are dissolved in 300 ml of ethyl acetate, and 19.2 g (0.10 mol) of 2-naphthoyl chloride and 16 ml (0.12 mol) of triethylamine are added, with stirring. After stirring for two hours at room temperature (RT), 300 ml of water are added and the separated organic phase is washed with 400 ml of dilute NaHCO$_3$ solution and finally with 200 ml of water. The organic phase is concentrated to one third of its volume and 200 ml of methanol are added, with stirring. Crystallization sets in immediately. After stirring for 16 hours at RT, the precipitate is filtered off with suction and then slurried with methanol. (−)-$\Delta^8$-6a,10a-Tetrahydrocannabinol 2-naphthoyl ester (15.1 g, 32.2 mmol; 43% based on olivetol) is obtained as a colorless crystalline powder after filtration.

EXAMPLE 2

Preparation of (−)-$\Delta^8$-6a,10a-trans-tetrahydrocannabinol ($\Delta^8$-THC)

22 ml of 2 N aqueous NaOH solution are added under argon to 15.43 g (33 mmol) of (−)-$\Delta^8$-6a,10a-trans-tetrahydrocannabinol 2-naphthoyl ester, prepared in Example 1, in 150 ml of THF and 25 ml of methanol. After vigorous stirring for a few hours, a further 25 ml of 1 N NaOH are added. After a total of 24 hours, 2.0 g (33 mmol) of glacial acetic acid are added for work-up and the reaction mixture is concentrated. The aqueous residue is taken up in 140 ml of water and extracted with 100 ml and 50 ml of MTBE (methyl tert-butyl ether), and the organic phase is extracted with 4-5 times 100 ml of semisaturated NaHCO$_3$ solution and finally washed with saturated NaCl solution. Drying over MgSO$_4$ and evaporation of the solvent yields approx. 10.7 g of an amber-colored oil (GC: >95% of $\Delta^8$-THC).

EXAMPLE 3

Preparation of (−)-$\Delta^9$-6a,10a-trans-tetrahydrocannabinol ($\Delta^9$-THC)

A) Preparation of (−)-9-chloro-6a,10a-trans-hexahydrocannabinol (THC HCl):

2.90 g of zinc chloride and 95 g of cold 30% HCl in ethyl acetate are added to 10.7 g of the (−)-$\Delta^8$-6a,10a-trans-tetrahydrocannabinol prepared in Example 2 and the mixture is warmed to RT, with vigorous stirring. After 36 hours, 100 ml of ethyl acetate and 200 ml of ice-water are added and the organic phase is washed with 200 ml of water and 7 ml of saturated sodium bicarbonate solution and with 100 ml of water and saturated NaCl solution. Drying (Na$_2$SO$_4$) and concentration/co-evaporation with 3 times 15 ml of MTBE (methyl tert-butyl ether) yields THC-HCl (12.42 g) as a dark oil.

B) Preparation of (−)-$\Delta^9$-6a,10a-trans-tetrahydrocannabinol ($\Delta^8$-THC)

5.74 g of the product prepared in section A), (−)-9-chloro-6a,10a-trans-hexahydro-cannabinol (THC-HCl), in 50 ml of MTBE (methyl tert-butyl ether) are added dropwise under argon at RT to 25 ml of a 1.7 N solution of K tert-pentylate (in toluene) in 30 ml of MTBE. After a total of one hour, the mixture is refluxed for 20-25 minutes and then cooled, 100 ml of MTBE are added and the mixture is extracted by shaking with 100 ml of saturated sodium bicarbonate solution and 2 ml of glacial acetic acid. The organic phase is washed with 100 ml of saturated NaCl solution, dried over Na$_2$SO$_4$ and concentrated to give 4.85 g of an amber-colored oil of the following composition [gas chromatographic analysis (GC)]: $\Delta^9$-THC: 87.6%, $\Delta^8$-THC: 4.7%, iso-THC: 5.4%.

EXAMPLE 4

Preparation of (−)-$\Delta^9$-6a,10a-trans-tetrahydrocannabinol 2-naphthoyl ester ($\Delta^9$ 2-naplith.)

3.95 g (21 mmol) of 2-naphthoyl chloride in 30 ml of ethyl acetate are added dropwise under argon to 5.90 g of the $\Delta^9$-THC prepared in Example 3 (86%/16.1 mmol) and 3.0 ml (22 mmol) of triethylamine in 50 ml of ethyl acetate. After stirring for 8 hours at RT, the mixture is washed with 50 ml of water, with 50 ml of semisaturated NaHCO$_3$ solution and with 50 ml of water. The organic phase is concentrated and the residue is crystallized from 20 ml of acetone and 40 ml of methanol. The 5.66 g of colorless crystals formed are recrystallized from acetone and methanol to give 4.47 g (9.5 mmol, 59%) of (−)-$\Delta^9$-6a,10a-trans-tetrahydrocannabinol 2-naphthoyl ester in the form of a white crystalline powder.

EXAMPLE 5

Preparation of (−)-$\Delta^9$-6a,10a-trans-tetrahydrocannabinol ($\Delta^9$-THC)

0.50 g (1.07 mmol) of the (−)-$\Delta^9$-6a,10a-trans-tetrahydrocannabinol 2-naphthoyl ester prepared in Example 4 is dissolved in 5 ml of THF and 0.7 ml of MeOH, and 0.7 ml of 2 N NaOH is added under argon. After stirring for 2 hours, a further 0.7 ml of 1 N NaOH is added. After a total of 9 hours, 20 ml of MTBE, 20 ml of semisaturated NaHCO$_3$ solution and 0.18 ml of glacial acetic acid are added. The organic phase is washed 4-5 times with NaHCO$_3$ solution and once with saturated NaCl solution, dried over Na$_2$SO$_4$ and concentrated to give 0.305 g (0.97 mmol) of (−)-$\Delta^9$-6a,10a-trans-tetrahydrocannabinol in the form of a yellowish oil; GC: $\Delta^9$-THC>99%, $\Delta^8$-THC<1.0%.

The invention claimed is:
1. Process for obtaining pure tetrahydrocannabinol from reaction mixtures containing tetrahydrocannabinol compounds or from crude product containing tetrahydrocannabinol compounds, characterized in that the tetrahydrocannabinol compound in the reaction mixture or in the crude product is converted to a crystallizable derivative of formulae (III) and (IIIA):

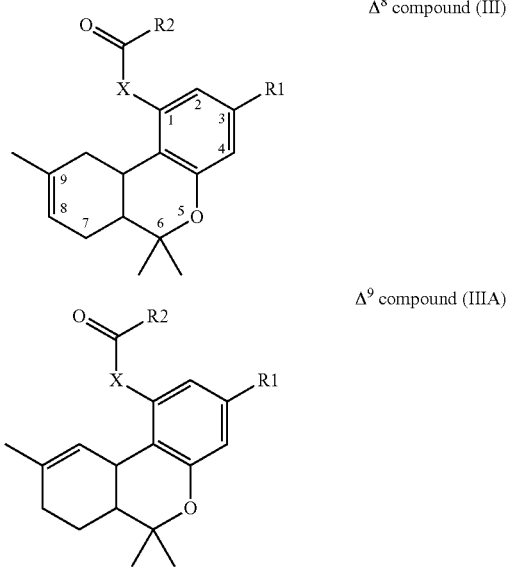

Δ⁸ compound (III)

Δ⁹ compound (IIIA)

in which
- R₁ is hydrogen, chlorine or (C₁₋₁₀)-alkyl;
- X is —O— (oxygen) or —NH—; and
- R₂ is an optionally substituted aliphatic or aromatic radical which optionally carries a substituent capable of salt formation; or a heterocyclic radical which optionally is itself capable of salt formation and/or optionally carries a substituent capable of salt formation; or a radical of an aliphatic or aromatic polybasic acid; whereby said derivative is crystallized out and isolated and the pure tetrahydrocannabinol compound is then obtained from the crystallized derivative.

2. Process according to claim 1, characterized in that pure Δ⁸-THC or Δ⁹-THC are obtained from a reaction mixture or crude product containing Δ⁸-THC and/or Δ⁹-THC.

3. Process according to claim 1, characterized in that compounds of formulae (I) and (IA) are prepared:

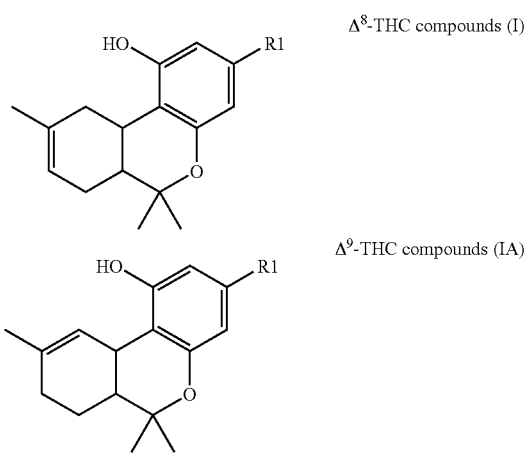

Δ⁸-THC compounds (I)

Δ⁹-THC compounds (IA)

in which R₁ is hydrogen, chlorine or (C₁₋₁₀)-alkyl.

4. Process according to claim 3, characterized in that compounds of formulae (I') and (I'A) are prepared:

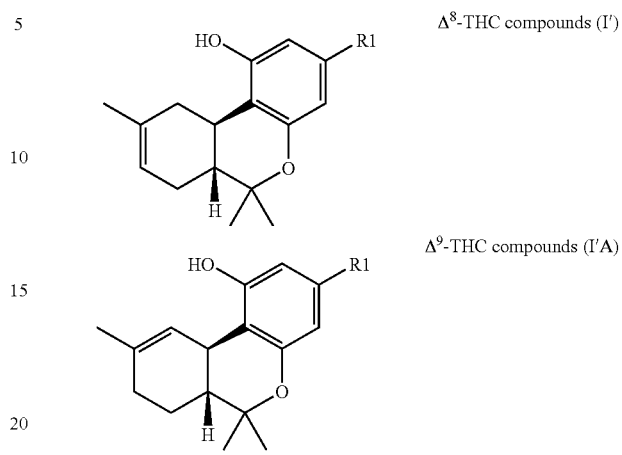

Δ⁸-THC compounds (I')

Δ⁹-THC compounds (I'A)

in which R₁ is hydrogen, chlorine or (C₁₋₁₀)-alkyl.

5. Process according to claim 1, characterized in that R₁ is n-C₅H₁₁.

6. The pure crystallizable and the crystallized tetrahydrocannabinol compounds prepared according to claim 1.

7. The compounds of claim 1 for the preparation of a drug for human therapy.

8. The drugs prepared according to claim 7.

9. Process according to claim 1, characterized in that X is —O—(oxygen).

10. Process according to claim 1, characterized in that R₁ is n-C₅H₁₁, and R₂ is phenyl optionally substituted by nitro, halogen, methyl or sulfonyl, or naphthyl, optionally substituted by nitro, halogen, methyl or sulfonyl.

11. Process according to claim 1, characterized in that R₁ is n-C₅H₁₁, and R₂ is unsubstituted naphthyl.

12. Process according to claim 1, characterized in that R₂ is a heterocyclic radical that is itself capable of salt formation or optionally carries a substituent capable of salt formation and is a 2-pyridyl, 3-pyridyl or 4-pyridyl derivative or a corresponding picoline, pyrazine, pyrazole, pyrrole or indole derivative.

13. Process according to claim 1, characterized in that R₂ is a substituent derived from pyridinecarboxylic acid or pyridine.

14. Process according to claim 1 characterized in that R₂ is a residue of phthalic acid or terephthalic acid, wherein the acid group not bonded to the THC derivative is optionally bonded to a radical capable of salt formation.

15. Process according to claim 1 characterized in that R₂ is a residue of 1-naphthoic acid, 2-naphthoic acid, 1-naphthylacetic acid or 2-naphthylacetic acid.

16. Process accordin. to claim 1 characterized in that R₂ is a residue of 9-anthracenecarboxylic acid or 9-phenanthrenecarboxylic acid.

17. Process according to claim 1, characterized in that stereospecifically (enantiomerically) pure Δ⁸-THC and stereospecifically (enantiomerically) pure Δ⁹-THC, are obtained from a reaction mixture or crude product containing Δ⁸-THC and/or Δ⁹-THC.

* * * * *